United States Patent
Daute et al.

(10) Patent No.: US 7,071,343 B2
(45) Date of Patent: Jul. 4, 2006

(54) METHOD FOR PRODUCING EPOXIDATED GLYCERIDE ACETATES

(75) Inventors: Peter Daute, Beverstadt (DE); Ralf Picard, Bremerhaven (DE); Joerg-Dieter Klamann, Bremerhaven (DE); Peter Wedl, Bremerhaven (DE); Artur Peters, Loxstedt (DE)

(73) Assignee: Cognis Deutschland GmbH & Co. KG, Duesseldorf (DE)

( * ) Notice: Subject to any disclaimer, the term of this patent is extended or adjusted under 35 U.S.C. 154(b) by 190 days.

(21) Appl. No.: 10/467,026

(22) PCT Filed: Jan. 23, 2002

(86) PCT No.: PCT/EP02/00618

§ 371 (c)(1),
(2), (4) Date: Jan. 8, 2004

(87) PCT Pub. No.: WO02/060884

PCT Pub. Date: Aug. 8, 2002

(65) Prior Publication Data

US 2004/0106812 A1    Jun. 3, 2004

(30) Foreign Application Priority Data

Feb. 1, 2001 (DE) .................. 101 04 815

(51) Int. Cl.
*C07D 301/27* (2006.01)
(52) U.S. Cl. ...................................... 549/514
(58) Field of Classification Search ................. 549/514
See application file for complete search history.

(56) References Cited

U.S. PATENT DOCUMENTS

| 2,895,966 A | 7/1959 | Ault et al. |
| 3,049,504 A | 8/1962 | Swem et al. |
| 4,381,407 A | 4/1983 | Bremus et al. |

FOREIGN PATENT DOCUMENTS

| DE | 30 04 660 A1 | 8/1981 |
| WO | WO 90/12858 A1 | 11/1990 |

*Primary Examiner*—Taofiq Solola
(74) *Attorney, Agent, or Firm*—Arthur G. Seifert; John F. Daniels

(57) ABSTRACT

Epoxidized glyceride acetates are made by a process which comprises reacting an epoxy fatty acid ester and triacetin.

9 Claims, No Drawings

METHOD FOR PRODUCING EPOXIDATED GLYCERIDE ACETATES

This invention relates to a process for the production of epoxidized glyceride acetates in which epoxy fatty acid esters are transesterified with triacetin.

In the processing, more especially the molding, of halogen-containing organic plastics, more particularly polyvinyl chloride (PVC), additives are generally incorporated in the plastics with the intention of performing certain functions. The additives may be required to develop their effect during processing itself or to impart certain properties to the moldings or workpieces thus obtained.

An important class of such additives which are widely used are the so-called plasticizers. As well-known to the expert, the plasticizer market has long been dominated by so-called phthalates or adipates. Dioctyl phthalate (DOP) and dioctyl adipate (DOA) in particular are routinely used as plasticizers.

However, there has long been a need to replace the traditional plasticizers mentioned, such as DOP or DOA, by plasticizers with a different structure. A technical solution to this problem was proposed in U.S. Pat. No. 2,895,966 published in 1959. This document proposes epoxidized monoglyceride diacetates, for example monoepoxystearyl diacetoglyceride, as plasticizers for plastics and states that, besides certain stabilizing properties, compounds such as these in particular have a plasticizing effect and, in addition, may readily be incorporated in numerous plastics, i.e. are compatible with those plastics.

According to U.S. Pat. No. 2,895,966, the plasticizers are produced by initially preparing monoglyceride diacetates based on unsaturated fatty acids and then subjected them to epoxidation. However, the plasticizers proposed in U.S. Pat. No. 2,895,966 were never successfully used in practice. A major reason for this may lie in the fact that they are difficult to produce on an industrial scale. According to the technical teaching disclosed in U.S. Pat. No. 2,895,966, an oil having a corresponding content of C=C double bonds in the fatty acid units is first subjected to transesterification with glycerol, followed by acetylation and finally—in a third step—by epoxidation. After each process step, the crude product obtained is elaborately purified. More particularly, the crude product obtained after the transesterification with glycerol is washed with water to remove any soap formed and glycerol. The crude product obtained after acetylation with excess acetanhydride is also washed with water in an inert gas atmosphere and then dried.

As for the rest, it is pointed out that the technical teaching of U.S. Pat. No. 2,895,966 is specifically directed to monoglyceride diacetates. This is particularly apparent from the paragraph linking columns 1 and 2. Although it is stated by way of limitation that complex mixtures of substances containing certain quantities of glycerides with only one aceto group are normally present, it is directly and clearly disclosed that monoglyceride diacetates in these mixtures are the critical and quantitatively dominant species for the effect to be obtained and for solving the stated problem.

DESCRIPTION OF THE INVENTION

The problem addressed by the present invention was to provide an improved process for the production of plasticizers for halogen-containing plastics of the epoxidized glyceride acetate type. Another problem addressed by the present invention was to provide active-substance mixtures of epoxidized glyceride acetates not disclosed in the prior art which would be particularly suitable as plasticizing substances for PVC by virtue of their specific composition.

In a first embodiment, the present invention relates to a process for the production of epoxidized glyceride acetates in which epoxyfatty acid esters are transesterified with triacetin.

Epoxidized Glyceride Acetates

In the process according to the invention, epoxyfatty acid esters are reacted with triacetin—a reaction which may be chemically interpreted as transesterification. The product present after this reaction need not necessarily be homogeneous in the sense of a single molecular structure. On the contrary, this product is generally a more or less complex mixture of different chemical individuals. Nevertheless, such a mixture is also referred to as "epoxidized glyceride acetate" in the present specification on pragmatic grounds. Depending on the desired reaction ratio of the two reactants of the transesterification (see below), epoxidized monoglyceride diacetates or epoxidized diglyceride monoacetates may represent quantitatively the dominant species of the product mixture.

Epoxyfatty Acid Esters

In the context of the present invention, epoxyfatty acid esters are understood to be:

a) Monoesters of fatty acids and monohydric alcohols with the formula $R^1$—OH, where $R^1$ is a $C_{1-18}$ alkyl group which may be saturated or unsaturated, linear or branched, aliphatic or cycloaliphatic, with the proviso that the fatty acid part derives from a $C_{8-24}$ fatty acid which contains at least one C=C double bond per molecule and with the further proviso that at least one C=C double bond per fatty acid unit is present in epoxidized form.

b) Triesters of fatty acids and glycerol, with the proviso that the fatty acid components derive from $C_{3-24}$ fatty acids, with the proviso that at least 30% of the fatty acid units of the triesters contain at least one C=C double bond and with the additional proviso that at least one C=C double bond per molecule of triester is present in epoxidized form.

The term "fatty acid" is familiar to the expert and is defined, for example, in the standard work Römpps Chemie-Lexikon (cf. 7th Edition, Stuttgart 1973, pages 1107–1110).

The compounds b) are triglycerides based on the fatty acids mentioned and glycerol. The glycerides used may be synthetically produced compounds or even fats and oils of natural origin (for a definition of "fats and oils", see for example Römpps Chemie-Lexikon, cf. 7th Edition, Stuttgart 1973, pages 1101–1106).

Preferably at least 50% and more particularly at least 80% of the fatty acid units of the triesters b) contain at least one C=C double bond.

The proviso that at least one C=C double bond per molecule of triester b) must be present in epoxidized form logically applies only to those molecules of the triester in which at least one C=C double bond is present because, although a triester b) by definition contains a certain proportion of fatty acid units with at least one C=C double bond, particularly where it derives from fats and oils of natural origin, molecules whose fatty acid units are all saturated may also be present in the triester on account of the statistical distribution.

Triacetin

Triacetin is characterized by the following structure:

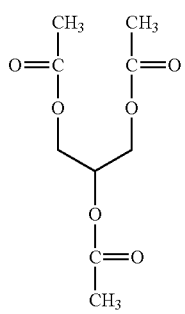

Triacetin is a commercially available product of which the production has long been known. For example, DE-A-30 04 660 describes a process for the production of triacetin by reaction of glycerol with acetic acid and acetic anhydride.

Transesterification of Epoxyfatty Acid Esters With Triacetin

The process according to the invention represents a transesterification reaction. In this reaction, the oxirane rings (=epoxide groups) of the epoxyfatty acid esters remain intact.

The process according to the invention is preferably carried out in the presence of a transesterification catalyst. Transesterification catalysts are known to the expert. They are preferably basic compounds, such as sodium hydroxide, potassium hydroxide, lithium hydroxide, sodium methylate, sodium ethylate, and also tin(IV) compounds such as, for example, dibutyl tin dilaurate. The quantities of catalyst used are preferably between 0.01 and 1.0% by weight, based on the total quantity of epoxyfatty acid esters and triacetin used, and more particularly between 0.05 and 0.2% by weight.

The process according to the invention is preferably carried out at reaction temperatures in the range from 120 to 240° C. and more particularly at reaction temperatures in the range from 150 to 230° C.

The reaction times in the process according to the invention are preferably 1 to 6 hours and more particularly 3 to 5 hours.

The molar ratios of epoxyfatty acid esters and triacetin in the process according to the invention are preferably adjusted to values of 1:2 to 2:1.

The epoxyfatty acid esters used in the process according to the invention are, in particular, epoxidized esters of fatty acids and monohydric alcohols of the type a) defined in more detail above, the alcohol units of these esters being selected from the group consisting of methanol, ethanol, propanol, butanol and 2-ethylhexanol;

soybean oil epoxide, linseed oil epoxide, sunflower oil epoxide, rapeseed oil epoxide, tallow epoxide.

The present invention also relates to epoxidized glyceride acetates obtainable by transesterification of epoxyfatty acid esters with triacetin in such a molar ratio that diglyceride monoacetates are quantitatively the dominant species in the product mixture. To this end, the molar ratios of epoxyfatty acid esters to triacetin are adjusted in the transesterification reaction to values of, in particular, 1.1:1 to 2:1.

The present invention also relates to the use of epoxidized glyceride acetates, which are obtainable by transesterification of epoxyfatty acid esters with triacetin in such a molar ratio that diglyceride monoacetates are quantitatively the dominant species in the product mixture, as plasticizers for halogen-containing organic plastics, more particularly PVC.

EXAMPLES

| Substances used | |
|---|---|
| Name | Explanation |
| Vinnolit ® H 70 DF | PVC (Advent International) |
| Irgastab ® BZ 561 | Ba/Zn stabilizer (Ciba-Geigy) |
| Edenol ® D 81 | Epoxidized soybean oil (Cognis/DE) |
| Stabiol ® CZ 222 | Ca/Zn stabilizer (Cognis/DE) |
| Loxiol ® G 10 | Lubricant (Cognis/DE) |
| Loxiol ® G 20 | Lubricant (Cognis/DE) |
| Dioctyl phthalate | Plasticizer (Degussa-Hüls/DE) |
| Dioctyl adipate | Plasticizer (Degussa-Hüls/DE) |

Production Examples

Example 1

Transesterification of Oleic Acid Methyl Ester Epoxide With Triacetin 145 g triacetin were transesterified with 205 g oleic acid methyl ester epoxide (epoxide content 4.9%) at 150° C. in the presence of 1.8 g sodium methylate as catalyst. The reaction time was 3 hours. Ca. 30 g acetic acid methyl ester were distilled off as secondary product. 320 g glycerol monoepoxyoleate diacetate were obtained. This product had the following characteristics:

| acid value (AV): | 0.97 |
|---|---|
| saponification value (SV): | 390 |
| epoxide content: | 3.1% |

If desired, the color of the product may be improved by bleaching with ca. 2 g hydrogen peroxide (30%).

Example 2

Transesterification of Epoxidized Soybean Oil With Triacetin 340 g epoxidized soybean oil (Edenol D 81) were transesterified with 161 g triacetin at 220° C. in the presence of 0.25 g sodium hydroxide as catalyst. The reaction time was 4 hours. To improve its color, the product was bleached with ca. 2 g hydrogen peroxide (30%). Ca. 500 g glycerol monoepoxyoleate diacetate were obtained. This product had the following characteristics:

| AV: | 0.86 |
|---|---|
| Lovibond color 1": | yellow: 5.6, red: 1.0 |
| epoxide content: | 4.1% |

Example 3

Transesterification of Epoxidized Soybean Oil With Triacetin 340 g epoxidized soybean oil (Edenol D 81) were transesterified with 161 g triacetin at 220° C. in the presence of 0.25 g dibutyl tin dilaurate as catalyst. The reaction time was 3 hours. To improve its color, the product was bleached with ca. 1 g hydrogen peroxide (30%). Ca. 500 g glycerol monoepoxyoleate diacetate were obtained. This product had the following characteristics:

| | |
|---|---|
| AV: | 1.2 |
| Lovibond color 1": | yellow: 6.2, red: 1.0 |
| epoxide content: | 4.0% |

Application Examples

Formulations F1 to F8 based on various plasticizers were produced for performance testing. The composition of these formulations is shown in the following Table.

The quantities in which the individual components are used are expressed in "phr" which stands for parts per hundred resin and indicates how many parts by weight of the particular substance are present in the PVC after addition of the composition, based on 100 parts by weight PVC. Accordingly, the formulations all contain 100 parts PVC (Vinnolit H 70 DF).

It is specifically pointed out that, in the case of F1 to F8, it is important to distinguish between the overall formulations, which are used for performance testing and which contain all the components mentioned, and the actual additive compositions which contain all the components mentioned except for the PVC.

| | F1 | F2 | F3 |
|---|---|---|---|
| Vinnolit H 70 DF | 100 | 100 | 100 |
| Irgastab BZ 561 | 1.5 | 1.5 | 1.5 |
| Dioctyl phthalate | 100 | 0 | 0 |
| Dioctyl adipate | 0 | 100 | 0 |
| Compound of Example 1 | 0 | 0 | 100 |

| | F4 | F5 | F6 |
|---|---|---|---|
| Vinnolit H 70 DF | 100 | 100 | 100 |
| Edenol D 81 | 8 | 8 | 8 |
| Stabiol CZ 2222 | 1 | 1 | 1 |
| Loxiol G 10 | 2.5 | 2.5 | 2.5 |
| Loxiol G 20 | 0.2 | 0.2 | 0.2 |
| Dioctyl phthalate | 30 | 0 | 0 |
| Compound of Example 2 | 0 | 30 | 0 |
| Compound of Example 3 | 0 | 0 | 30 |

| | F7 | F8 |
|---|---|---|
| Vinnolit H 70 DF | 100 | 100 |
| Edenol D 81 | 8 | 8 |
| Stabiol CZ 222 | 1 | 1 |
| Loxiol G 10 | 2.5 | 2.5 |
| Loxiol G 20 | 0.2 | 0.2 |
| Dioctyl adipate | 50 | 0 |
| Compound of Example 3 | 0 | 50 |

Strips were produced on the basis of formulations R1 to R8 and were tested for static thermal stability at 180° C. The strips were produced by homogenizing and plasticizing the formulations mentioned for 5 mins. at 170° C. on laboratory rolls. Test specimens measuring 17×17 mm were cut out from the ca. 0.5 mm thick strips thus produced.

The following measurements were carried out with the test formulations:

Stability test at elevated temperature: strips were produced from the formulations and tested for static thermal stability at 180° C. The strips were produced by homogenizing and plasticizing the components of the formulations mentioned for 5 mins. at 170° C. on laboratory rolls. Test specimens measuring 17×17 mm were cut out from the ca. 0.5 mm thick strips thus produced. The test specimens arranged on glass plates were placed on rotating shelves in a heating cabinet at 180° C. and removed at 15-minute intervals until all the test specimens were "burnt" (i.e. had turned black in color).

Color measurement of strips: in addition, the L*, a*, b* method known to the expert (cf. DIN 6174) was applied to the strips for further characterization. The initial color of the strip (yellowness value b*) was determined. A commercially available instrument ("Micro Color", manufacturer: Dr. B. Lange) was used for the measurements.

Shore A hardness: the Shore A hardness of the strips as known to the relevant expert was determined to DIN 52505 using a commercially available Shore hardness tester (manufacturer: Zwick).

Light transmission: the light transmission of 4 mm thick pressed plates based on the formulations mentioned was determined. The pressed plates were produced from the strips. The strips were pressed between two pressing plates of a laboratory press (Collin) with spacers in between to form plates with the thickness mentioned. In the tests carried out, 8 strips each 0.5 mm thick were pressed at 170° C./250 bar to form a 4 mm thick pressed plate.

Compatibility: by compatibility is meant the compatibility of the additive compositions with the plastic (PVC). The compatibility of the strips was determined after storage at room temperature. The strips were tested for compatibility by visual examination. The surface of the strip was evaluated for signs of exudation. In this method, serious exudation is an indicator of serious incompatibility; the absence of exudation is an indicator of very good compatibility.

The results obtained with the test specimens are set out in the following Table. C1 is a test specimen based on additive composition R1, C2 is a test specimen based on additive composition F2, etc.

| | C1 | C2 | C3 |
|---|---|---|---|
| Thermal stability (180° C.) | 75 mins. | 60 mins. | >270 mins. |
| Shore A hardness | 61 | 58 | 65 |

-continued

| | | | |
|---|---|---|---|
| Transparency (light transmission in %, 4 mm pressed plate) | 83 | 76 | 83 |
| Compatibility after production | Very good, no exudation, | Very good, no exudation | Very good, no exudation |
| Compatibility after 6 months (storage at room temperature) | Very good, no exudation | Very good, no exudation | Very good, no exudation |
| Compatibility after 12 months (storage at room temperature) | Very good, no exudation | Very good, no exudation, | Very good, no exudation |

| | C4 | C5 | C6 |
|---|---|---|---|
| Thermal stability (180° C.) | 90 mins. | 210 mins. | 210 mins. |
| Shore A hardness | 90 | 93 | 93 |
| Initial color of the strip (yellowness value b*) | 4.7 | 6.3 | 5.8 |
| Compatibility after production | Very good, no exudation, | Very good, no exudation | Very good, no exudation |
| Compatibility after 18 months (storage at room temperature) | Very good, no exudation | Very good, no exudation | Very good, no exudation |

| | C7 | C8 |
|---|---|---|
| Thermal stability (180° C.) | 75 mins. | 240 mins. |
| Shore A hardness | 73 | 80 |
| Initial color of the strip (yellowness value b*) | 2.6 | 4.3 |
| Compatibility after production | Very good, no exudation | Very good, no exudation |
| Compatibility after 10 weeks (storage at room temperature) | Very good, no exudation | Very good, no exudation, |

The invention claimed is:

1. A process for the production of an epoxidized glyceride acetate which comprises reacting an epoxy fatty acid ester and triacetin.

2. The process of claim 1 wherein the epoxy fatty acid ester is a triester of a fatty acid and glycerol wherein the fatty acid components of the triester are derived from $C_{3-24}$, fatty acids, with the proviso that at least 80% oft. fatty add units of the triesters contain at least one C=C double band and with the additional proviso that at least one C=C double bond per molecule of triester is present in epoxidized form.

3. The process of claim 1 wherein the process is carried oat in the presence of a transesterification catalyst.

4. The process of claim 3 wherein the catalyst is used in a quantity of from 0.01 to 1.0% by weight, based on the total quantity of epoxy fatty acid ester used and triacetin.

5. The process of claim 1 wherein the process is carried out at a temperature of from 120 to 240° C.

6. The process of claim 1 wherein the process is carried out in a time period of from 1 to 6 hours.

7. The process of claim 1 wherein the mole ratio of epoxy fatty acid ester to triacetin is from 1:2 to 2:1.

8. A process for the production of a product comprising a major amount of an epoxidized diglyceride acetate which comprises reacting an epoxy fatty acid ester and triacetin wherein the molar ratios of epoxy fatty acid esters to triacetin is from 1:2 to 2:1.

9. A method of plasticizing a halogen-containing plastics comprising adding to a halogen-containing plastic a plasticizing-effective amount of a compound of claim 8.

* * * * *